(12) United States Patent
Morgan et al.

(10) Patent No.: US 7,924,425 B2
(45) Date of Patent: Apr. 12, 2011

(54) SPATIALLY SELECTIVE FIXED-OPTICS MULTICOLOR FLUORESCENCE DETECTION SYSTEM FOR A MULTICHANNEL MICROFLUIDIC DEVICE, AND METHOD FOR DETECTION

(75) Inventors: Nicole Y. Morgan, Bethesda, MD (US); Paul Smith, Annapolis, MD (US); Ed Wellner, Fairfax, VA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 523 days.

(21) Appl. No.: 11/993,852

(22) PCT Filed: Jun. 26, 2006

(86) PCT No.: PCT/US2006/024751
§ 371 (c)(1),
(2), (4) Date: Dec. 21, 2007

(87) PCT Pub. No.: WO2007/002560
PCT Pub. Date: Jan. 4, 2007

(65) Prior Publication Data
US 2010/0165339 A1 Jul. 1, 2010

(51) Int. Cl.
*G01N 21/00* (2006.01)
(52) U.S. Cl. .................. 356/440; 356/317; 356/318
(58) Field of Classification Search .................. 356/317, 356/440, 318, 441
See application file for complete search history.

(56) References Cited

U.S. PATENT DOCUMENTS

| 6,028,306 | A | 2/2000 | Hayashi |
| 6,184,990 | B1 | 2/2001 | Amirkhanian et al. |
| 6,704,104 | B2* | 3/2004 | Li ................................. 356/317 |
| 7,002,671 | B2* | 2/2006 | Tsien et al. .................... 356/72 |
| 7,057,726 | B2* | 6/2006 | Hooper et al. ................ 356/417 |
| 2003/0116436 | A1 | 6/2003 | Amirkhanian et al. |

FOREIGN PATENT DOCUMENTS

| EP | 0587281 A2 | 3/1994 |
| EP | 0 973 040 A2 | 1/2000 |
| WO | WO-01/69211 A1 | 9/2001 |
| WO | WO-2006/027590 A3 | 11/2006 |

* cited by examiner

*Primary Examiner* — L. G Lauchman
(74) *Attorney, Agent, or Firm* — Polsinelli Shughart PC; Teddy C. Scott, Jr.; Paul A. Jenny

(57) ABSTRACT

A system for spatially selective, fixed-optics fluorescence detection in a multichannel polymeric microfluidic device, and a method for performing spatially selective, fixed-optics fluorescence detection.

34 Claims, 13 Drawing Sheets

PRESENT INVENTION

SPATIALLY SELECTIVE FIXED-OPTICS MULTICOLOR FLUORESCENCE DETECTION SYSTEM FOR A MULTICHANNEL MICROFLUIDIC DEVICE, AND METHOD FOR DETECTION

BACKGROUND OF THE INVENTION

1. Field of the Invention

The present invention relates to a system for spatially selective, fixed-optics fluorescence detection in a multichannel polymeric microfluidic device, and a method for performing spatially selective, fixed-optics fluorescence detection.

2. Description of Background Art

A promising analytical tool for analyzing biomolecules such as DNA, proteins and protein complexes in a biomedical or clinical laboratory is a microfluidic device. Microfluidic devices are characterized by having one or more channels with at least one dimension less than 1 mm (typically much less than 1 mm). Common fluids used in microfluidic devices include biofluids such as whole blood samples, bacterial cell suspensions, protein or antibody solutions and various buffers. Microfluidic devices can be used for a variety of measurements including molecular diffusion coefficients, fluid viscosity, pH, chemical binding coefficients and enzyme reaction kinetics. Other applications for microfluidic devices include capillary electrophoresis, isoelectric focusing, immunoassays, flow cytometry, injection of protein samples for analysis via mass spectrometry, DNA analysis, cell manipulation, cell separation, cell patterning and chemical gradient formation. Many of these applications have utility for clinical diagnostics.

The use of microfluidic devices to conduct biomedical research and create clinically useful technologies has a number of significant advantages. First, because the volume of fluids within these channels is very small, generally submicroliter, the amount of reagents and analytes used is quite small. This is especially significant for expensive reagents or samples.

Microfluidic devices can be fabricated using processes developed for the microelectronics industry to create tiny chambers and fluidic networks in quartz, silica, glass, or polymeric chips. Another advantage is that the fabrication techniques used to construct microfluidic devices are very amenable both to highly elaborate, multiplexed devices and also to mass production. Polymeric or plastic microfluidic devices have the additional advantage of being relatively inexpensive to manufacture. In a manner similar to that for microelectronics, microfluidic technologies enable the fabrication of highly integrated devices for performing several different functions on the same substrate chip.

Microfluidic devices can direct the flow of liquid chemical reagents similar to the way semiconductors direct the flow of electrons. Reagents can be diluted, mixed, or reacted with other reagents prior to analysis by capillary electrophoresis or electrochromatography—all on a single chip. As such, microfluidic devices can be designed to accommodate virtually any analytic biochemical process. Plastic, or polymeric, microfluidic devices are particularly attractive because of the low cost and relative ease of manufacture compared to glass devices. However, laser-induced fluorescence detection in polymeric microchips presents some unique challenges. Because a plastic substrate (in which the microchannels are formed) is substantially more fluorescent than freestanding silica capillaries, spatial selection is required to isolate the fluorescent signal originating from within the microchannel from fluorescence originating in the substrate material. In the past, this has typically been achieved with a confocal system; measurement of multiple channels then requires mechanical scanning of the optical elements. Examples of two different conventional laser-induced fluorescence detection systems are shown in FIGS. 1(a) and (b).

FIG. 1(a) shows a conventional confocal arrangement from Leica Microsystems (http://www.confocal-microscopy.com/website/sc_llt.nsf). In the confocal microscope shown all structures out of focus are suppressed at image formation. This is obtained by an arrangement of diaphragms, which, at optically conjugated points of the path of rays, act as a point light source and as a point detector respectively. Rays from out-of-focus areas are suppressed by the detection pinhole. The depth of the focal plane is, besides the wavelength of light, determined in particular by the numerical aperture of the objective used and the diameter of the diaphragm. With a wider detection pinhole the confocal effect can be reduced. To obtain a full image, the image point is moved across the specimen by mirror scanners. The emitted/reflected light passing through the detector pinhole is transformed into electrical signals by a photomultiplier and displayed on a computer monitor screen.

Typically, confocal arrangements, such as that shown in FIG. 1(a), would need to be augmented with additional optics behind the pinhole to direct light onto the detector(s), especially if multiple spectral bands were being examined. Thus, such a system is complex and includes moving parts.

FIG. 1(b) shows a conventional ball lens—optical coupling arrangement, with a 2 mm diameter ball lens 110 and a 1 mm core diameter fiber 60, and the ball lens 110 positioned to collimate light from source S. One advantage of a ball lens system over a confocal system is simplicity in assembly and alignment, as well as compactness. However, as can be seen in FIG. 1(b), the working distance d2 is very short, thus making this arrangement unsuitable in many situations. Further, if a conventional ball lens system were used in an epi-illumination setup for measurements on a plastic microfluidic device, the background fluorescence from the substrate would severely limit the sensitivity.

In sum, while plastic microchips remain attractive because of the low cost and relative ease of manufacture compared to glass systems, many drawbacks exist in using plastic microchips with conventional laser-induced fluorescence detection systems.

Accordingly, modern technology requires new detection systems that are simple and inexpensive to construct and operate, particularly when performing multiplexed measurements, in microchips with multiple channels.

BRIEF DESCRIPTION OF THE DRAWINGS

The present invention will become more fully understood from the detailed description given herein below and the accompanying drawings, which are given by way of illustration only, and thus are not limitative of the present invention.

DETAILED DESCRIPTION OF THE PREFERRED EMBODIMENTS

Features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings. It is to be understood that any particular embodiment of the invention may not exhibit every one of the advantages, nor achieve every object, of the invention.

It is to be understood that both the foregoing general description and the following detailed description of the invention are exemplary and explanatory of the invention as claimed. The scope of the invention is defined by the claims.

Accordingly, the present invention is directed to a system and method for sensitive, spatially resolved and spectrally resolved laser-induced fluorescence detection from multiple microfluidic channels that substantially obviates one or more problems due to limitations and disadvantages of the related art. Any particular embodiment of the invention might not solve every problem of the related art described above.

One embodiment of the present invention involves simultaneous detection from a plurality of microchannels in a plastic microchip for DNA analysis. Multiple colors of fluorescence may be detected in each microchannel. The detector of the present invention may be applied to fluorescence or luminescence detection for any microchip-based analysis in any transparent substrate.

The apparatus of the invention is robust, versatile, and contains only fixed optical parts. The economies of parallel analysis and the importance of spatial selectivity make the method of the present invention very useful for polymeric substrates with multiple microchannels. As mentioned earlier, spatial selectivity is important because plastic or polymeric materials tend to be fluorescent; thus there is a need to isolate signal originating from the analytic channel from fluorescence of substrate material. Parallel detection permits the running of multiple analyses simultaneously, thereby increasing throughput, and saving instrument and operator time.

Configuration for Detecting Fluids in a Single Channel

Figure 1A:
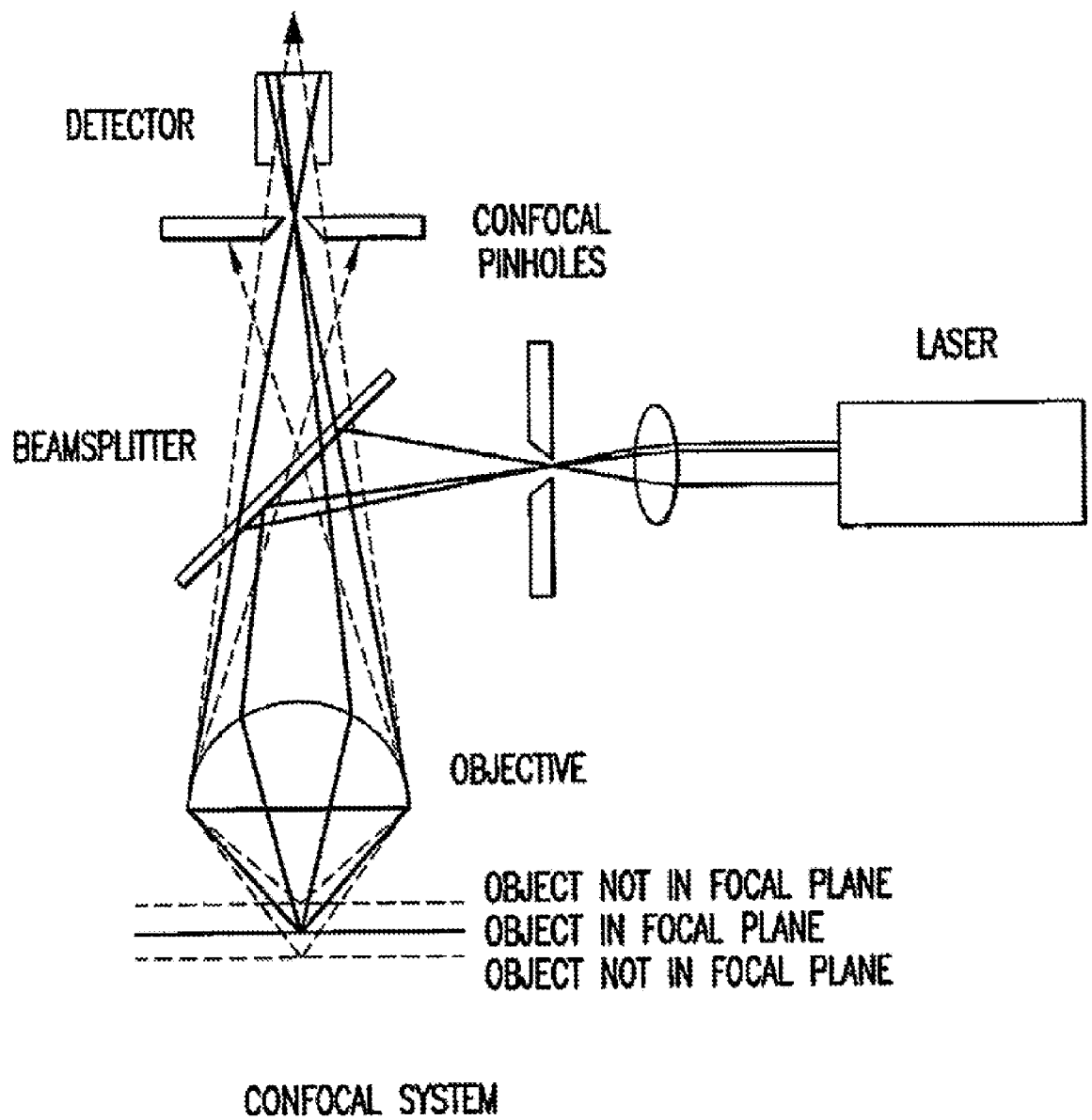
FIG. 1(a) is a schematic showing a conventional confocal lens arrangement known in the related art.
Figure 1B:
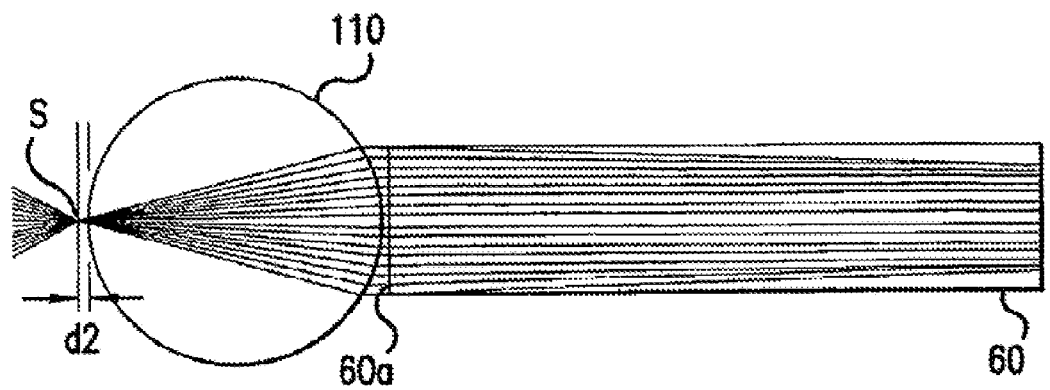
FIG. 1(b) is a schematic showing a conventional ball lens-optical fiber coupling arrangement known in the related art.
Figure 1C:
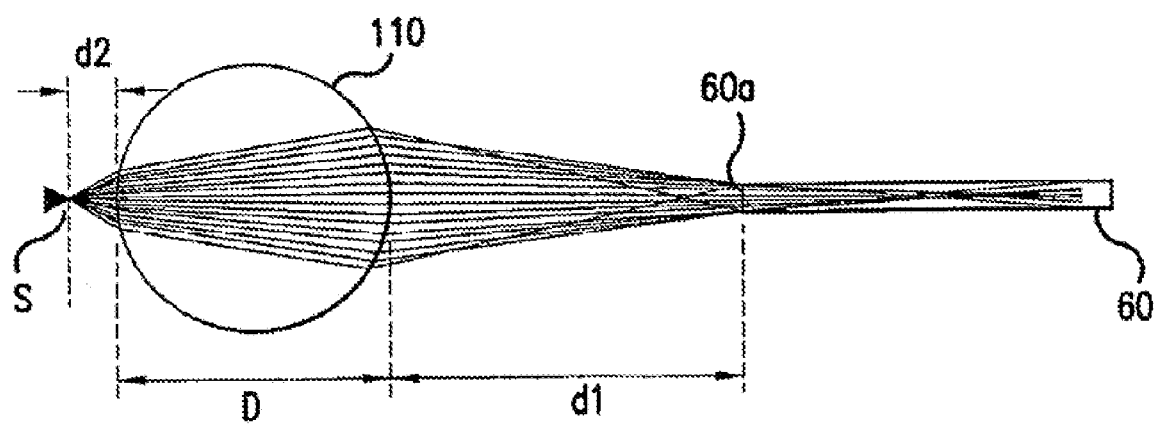
FIG. 1(c) is a schematic showing a ball lens-optical fiber coupling arrangement of the present invention.

The detection configuration of the present invention is depicted in FIGS. 1(c) and 2. A single microchannel is shown for simplicity.

FIG. 1(c) shows the quasi-focusing configuration of the present invention, with a 200 μm diameter fiber 60, the ball lens 110 and fiber 60 being separated by distance d1 in the axial direction of the fiber. The distance d1 from the ball lens 110 to the optical fiber 60 is determined by treating the sample S as a point source and positioning the ball lens 110 relative to the sample such that a circle of light defined by the intersection of a marginal transmitted ray and the caustic (the caustic being the envelope of the transmitted rays) has a diameter equal to that of the optical fiber 60, and the angle of the marginal transmitted ray as it enters the optical fiber is equal to the maximum acceptance angle of the optical fiber 60.

By comparing FIGS. 1(b) and 1(c), it will become apparent that the working distance d2 (i.e., distance in the axial direction between source S and ball lens 110) with the conventional ball lens—optical fiber coupling arrangement is substantially smaller than working distance d2 with the ball lens—optical fiber coupling arrangement of the present invention. Although, as shown in FIG. 1(b), more light can be collected using the conventional configuration using a large-diameter fiber 60, coupling light from this fiber into a spectrograph is not efficient. Further, in the conventional configuration, using a fiber with a diameter smaller than 1 mm (so as to match the spatial and spectral resolution desired with the spectrograph) would result in much less light being collected, as can be seen from the ray diagram in FIG. 1(b). Further, there is substantially less spatial selectivity in the axial direction using the conventional configuration than for the quasi-focusing configuration of FIG. 1(c).

Further, as can be seen in FIG. 1(c), the ball lens system of the present invention does not have a single focus; light transmitted up the fiber 60 comes from rays that converge at different points along the axis of the fiber 60 due to spherical aberrations. The present configuration takes advantage of the spherical aberrations inherent in ball lenses to collect more light into the fiber.

Figure 2A:
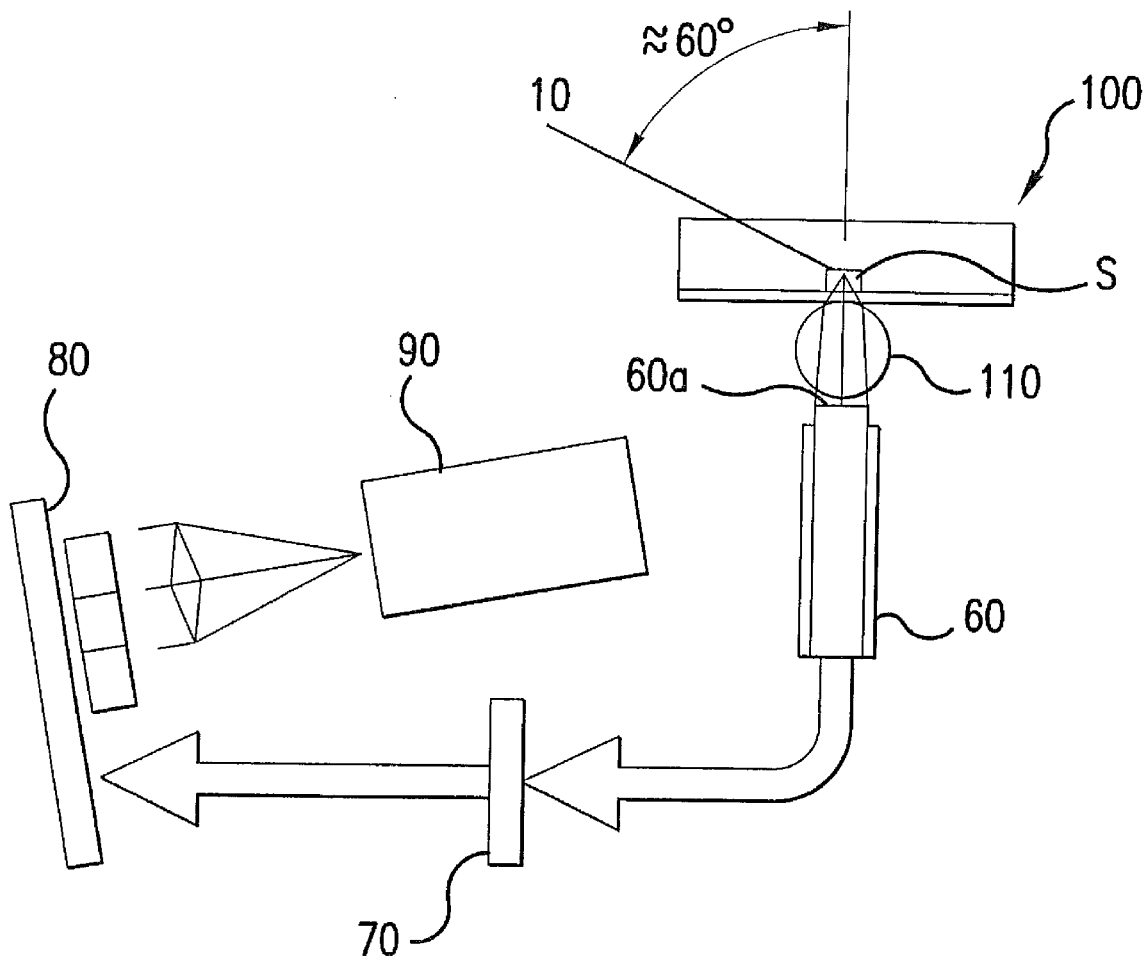
FIG. 2(a) is a schematic of excitation and detection components of the present invention for exciting and detecting fluorescence in a single channel.

Referring to FIG. 2(a), a free space laser excitation 10 is focused on a selected volume or sample (source) S located in a central volume of microchannel 50 in a microfluidic device (microchip) 100. Incidentally, the selected volume S has a height and width comparable to those of the microchannel 50, and the microchannel 50 is positioned such that light intensity from the selected volume S is maximized. In practice, this will involve moving the channel 50 slightly farther away from the ball lens 110 relative to the point source position used when determining the ball lens—fiber spacing. A 2 mm diameter ball lens 110 focuses emitted fluorescence onto a 0.22 NA 200 μm optical fiber 60, where NA=numerical aperture. The 2 mm ball lens 110 may be made out of LaSFN9, for example. LaSFN9 is a type of glass having a relatively high index of refraction (~1.85). Other materials/glasses may also be used, though the higher-index (i.e., more refractive) materials may collect more light.

After the detected light passes through a long pass filter 70 (An Omega Optical, 510AELP, for example), the signal is spectrally dispersed with an imaging spectrograph 80 (An Oriel FICS, for example) and the spectra are recorded with a camera 90, which preferably is a charged-coupled device, and preferably is cooled to minimize noise and increase sensitivity. (A QImaging Retiga EXI camera, for example). The camera 90 converts the optical signal into an electronic signal.

Cooling reduces electronic noise in the camera 90, and therefore greatly increases the sensitivity. Maximizing sensitivity while minimizing background noise is important for the camera 90, as these parameters directly impact the sensitivity and dynamic range of the measurement. Using a lower-quality detector is possible, but may be undesirable for some scientific applications.

As can be seen in FIG. 2(a), free space laser excitation 10 incident off-axis (~60 degrees to normal on the chip) is used to minimize the coupling of laser light into the aperture 60a of detection optical fiber 60. Angles other than ~60 degrees to normal may be used, so long as direct transmission of laser excitation into the detection optical fiber 60 is avoided. For the 200 μm fiber 2 mm ball lens configuration shown, this requires an angle greater than 30 degrees to normal. If the angle with respect to normal is too large (>80 degrees, for example), the laser spot size as it intersects the channel 50 can be larger than desired, and excite areas of the substrate outside the channel. Further, alignment becomes difficult, as the lateral position of the spot at the channel depth is more sensitive to variations in the substrate thickness.

The emitted fluorescence is detected with an optical fiber-ball lens combination. As described above, generally, the higher the refractive index of the ball lens 110 (for example, 1.85), the more light will be collected. A smaller diameter optical fiber 60 (50-150 μm) could also be used, resulting in greater spatial selectivity, especially in the lateral direction, but a smaller overall signal. An optical fiber 60 with a larger diameter (up to ⅓ the diameter of ball lens 110, for example) could also be used, resulting in more overall signal, but less spatial discrimination. Generally, to provide spatial selectivity in the lateral (i.e., off-axis) dimension, the fiber diameter should not be more than approximately 10 times larger than the lateral width of the channel. Optimal spatial selectivity in this lateral dimension will be achieved with a fiber diameter no more than a few times wider than the channel.

Choosing a higher-numerical aperture (NA) fiber in the present embodiment would result in loss of collected light at the spectrometer entrance without a substantial gain in the numerical aperture of the ball lens-fiber system. However, if a spectrometer/camera were not used as the detector, a higher-NA fiber 60 would collect slightly more light. Also, in applications where only one spectral band is measured, a spectrograph would not be required at all, and a higher NA is appropriate.

The resulting spectra are imaged using a cooled monochrome CCD camera 90 at 10 frames per second, which in the present embodiment is sufficient to detect ~10 pM fluorescein (FAM). The number of frames per second is data driven. It would be desirable to record multiple (>3-5) points per analyte peak; thus the desired number of frames per second is largely a question of the sample flow rate (e.g., how fast the peaks pass by the detection point).

Representative Experimental Results

Figure 2B:
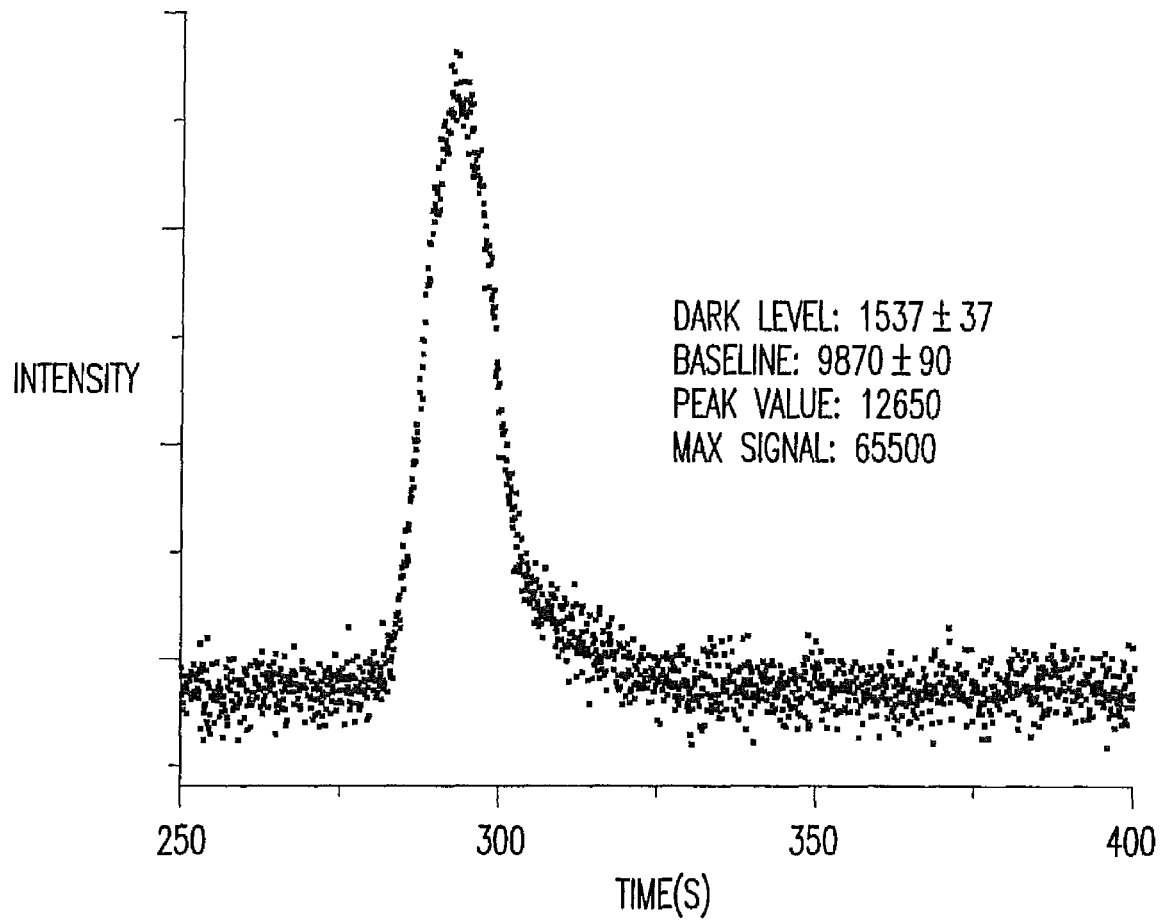
FIG. 2(b) illustrates a limit of detection for dye in a single polymeric microchannel for the fluorescence detection system of the present invention.

FIG. 2(b) illustrates representative experimental results showing the limit of detection for fluorescein in a single channel of the fluorescence detection system of the present invention.

The parameter of the experiment conducted were as follows:
Run buffer: 1.5% hydroxyethylcellulose in 1×TTE (50 mM Tris, 50 mM TAPS, 2 mM EDTA)+7M urea, pH 8.4
Sample buffer: 1×TTE+7M urea, pH 8.4
Temperature: 20° C.;
Separation field: 180 V/cm;
Chip: Hot-embossed medical grade PMMA, sealed with 30 μm laminate (12 μm PP, 15 μm LDPE/EVA co-polymer resin), in which
EDTA=Ethylenediaminetetraacetic Acid,
PMMA=Polymethylmethacrylate,
LDPE=low-density polyethylene, and
EVA=Ethylene Vinyl Acetate.

As shown in FIG. 2(b), an injected plug of 100 pM of fluorescein in a single channel was measured with S/N ~30, giving a limit of detection of 10 pM, with a 10 Hz data acquisition rate.

Extension to Multiple Channels

Next, referring to FIGS. 3(a) and (b), 4(a) and (b), 5(a) and (b), 6(a) and (b), 7 and 8, a multichannel configuration of the present invention will be described.

Figure 3A:
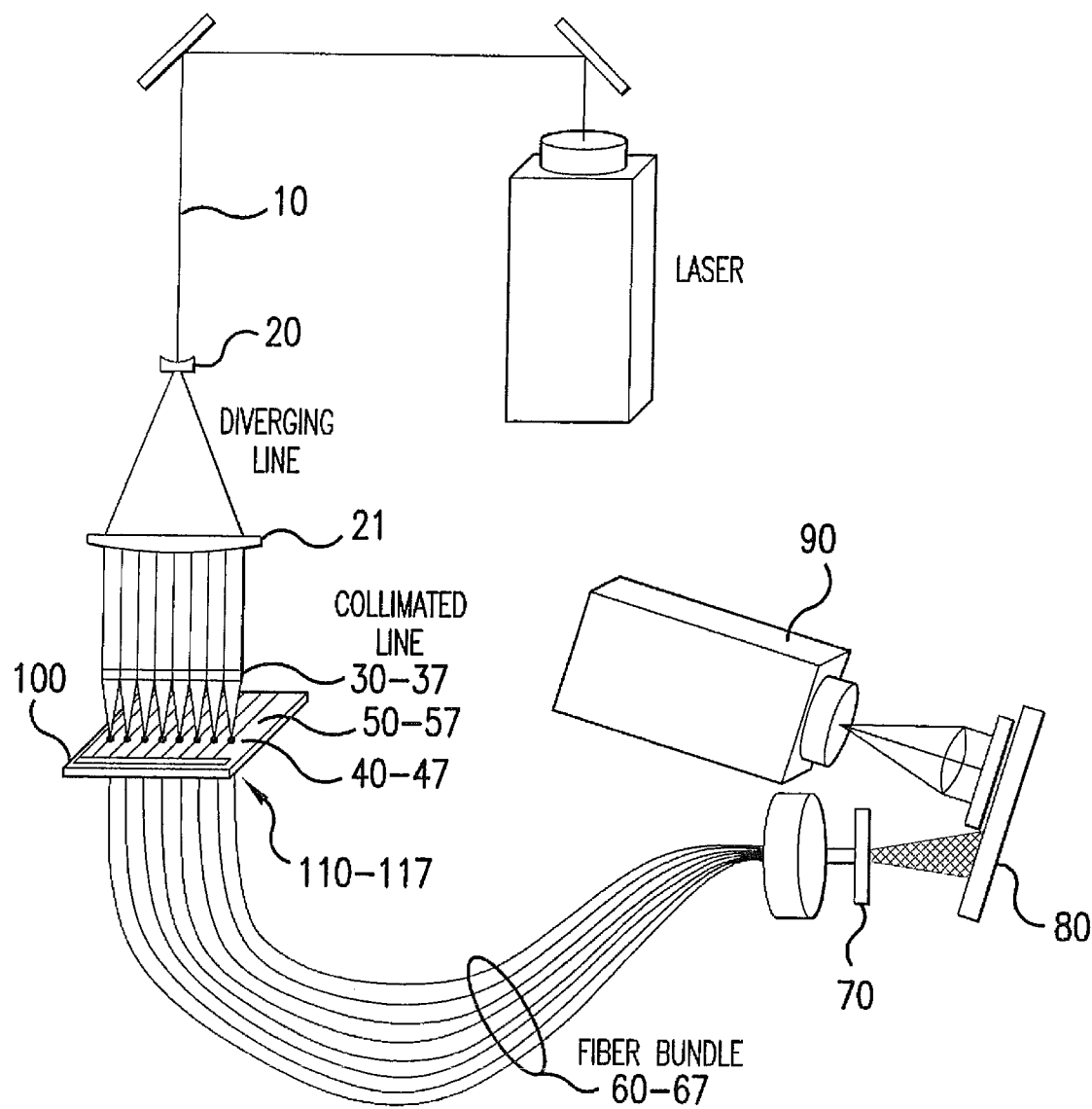
FIG. 3(a) is a schematic for separation of a single laser excitation beam into eight spots using two cylindrical lenses and an array of eight plano-convex lenses for use in a eight channel detection system.
Figure 3B:
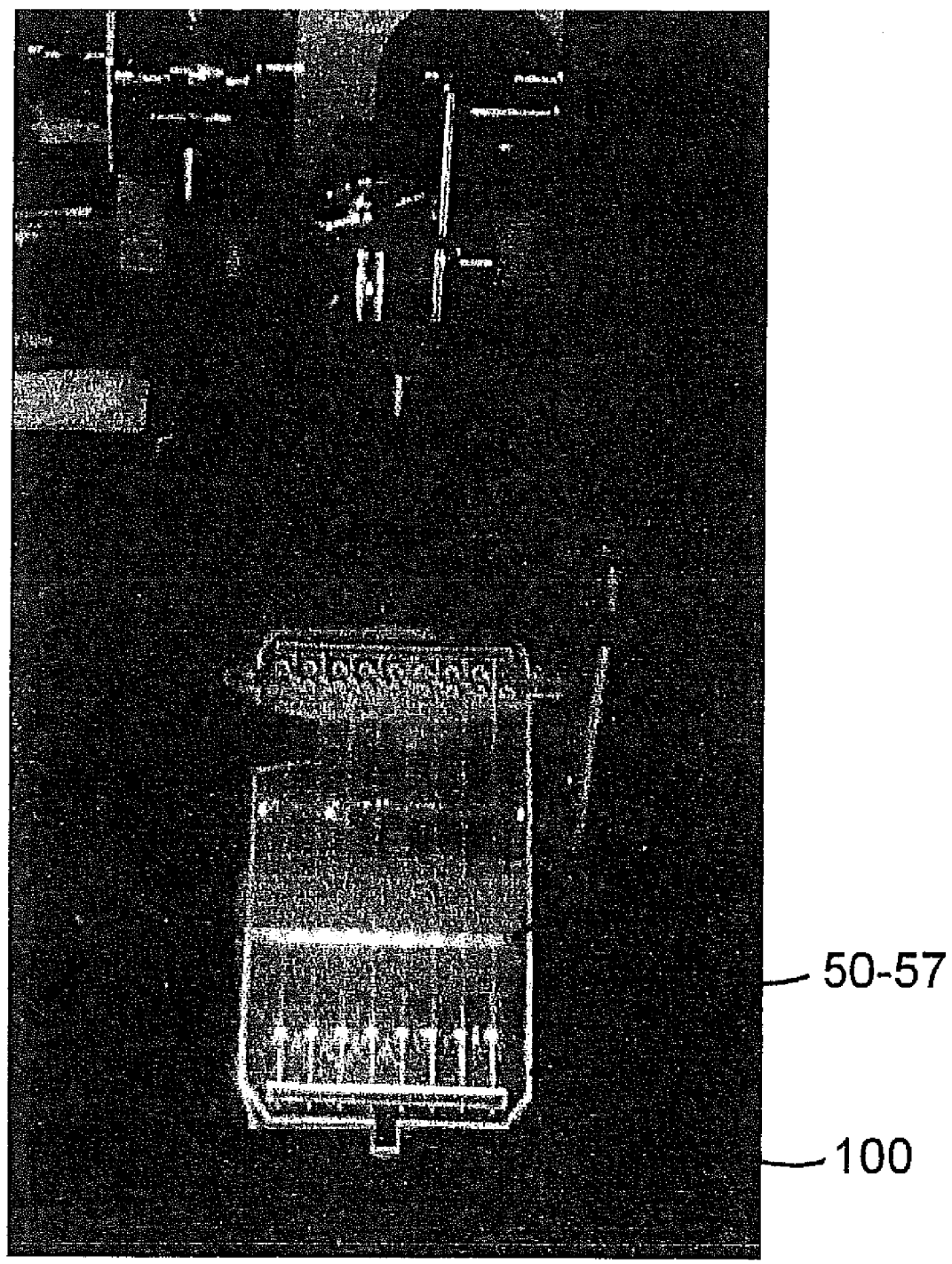
FIG. 3(b) illustrates the use of such lenses to generate eight focused spots onto an eight channel microfluidic device from a single 633 nm laser beam.

As shown in FIG. 3(a), a single laser excitation beam can be split into eight spots using two cylindrical lenses and an array of eight plano-convex lenses for use in an eight-channel detection system. FIGS. 3(b) illustrates a representative 633 nm laser beam generating eight focused spots onto an eight-channel microfluidic device from a single laser beam. In particular, FIG. 3(a) illustrates a single laser excitation 10 split into multiple (eight) spots 40-47 using two cylindrical lenses 20, 21 and an array of (eight) plano-convex lenses 30-37. The spacing of the plano-convex lenses 30-37 is chosen such that the eight laser spots 40-47 coincide with the eight microchannels 50-57 in the microchip 100. At each excitation spot 40-47, a ball lens 110-117, and optical fiber 60-67 is positioned underneath the corresponding microchannel 50-57. The emitted fluorescence is detected with an optical fiber-ball lens combination, via the one ball lens 110-117 and optical fiber 60-67 corresponding to each microchannel 50-57.

The 200 μm fiber diameter and 0.22 numerical aperture were chosen to give the desired spectral and spatial resolution in the multiple channel configuration such that eight spectra could fit in the imaging region of the spectrograph, and to match the acceptance angle of the spectrometer 80, respectively. The spatial selectivity is achieved by using a high refractive index 2 mm ball lens 110-117 and a small-diameter (200 μm) 0.22 NA optical fiber positioned to obtain focused light from each microchannel 50-57. The multiple channel configuration shown in FIGS. 3(a) and (b) is both more robust and more versatile than a conventional scanning system shown in FIG. 1(a), since there are no moving parts.

The detection optics of the present invention can be freely positioned near each microchannel 50-57 placing minimal constraints on channel layout and design. After the emitted fluorescence is coupled into the fiber 60-67, the light is passed through the long pass filter 70, and then spectrally dispersed using a compact imaging spectrograph 80.

For detection in the multiple channel configuration (see FIG. 3(b)), each microchannel 50-57 has a corresponding 2 mm ball lens 110-117 (as shown in FIG. 3(a)) and optical fibers 60-67 (as shown in FIG. 3(a)) in the desired orientation. For laser excitation in this particular multichannel embodiment (see FIG. 3(a)), one plano-convex lens 30-37 in the array is associated with each microchannel 50-57. The spacing of the plano-convex lenses 30-37 is equal to the spacing of the microchannels 50-57. Assuming the microchannels 50-57 are equally spaced with respect to each other, ideally, the diameter of each plano-convex lens 30-37 in the array will be exactly equal to the distance between adjacent microchannels, so that there is no gap between the plano-convex lenses 30-37.

Figure 4A:
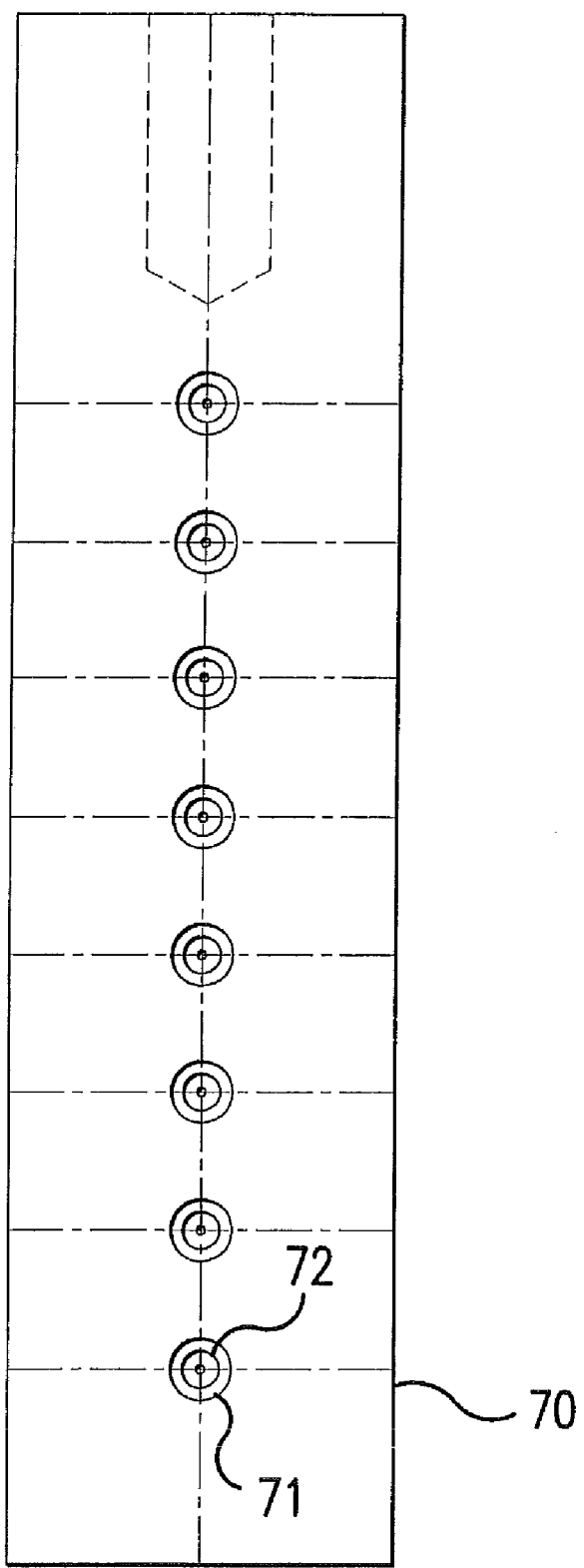
FIGS. 4(a) and (b) are top down and side views of a holder for eight ball lenses and eight optical fibers for detecting luminescence or fluorescence.
Figure 4B:
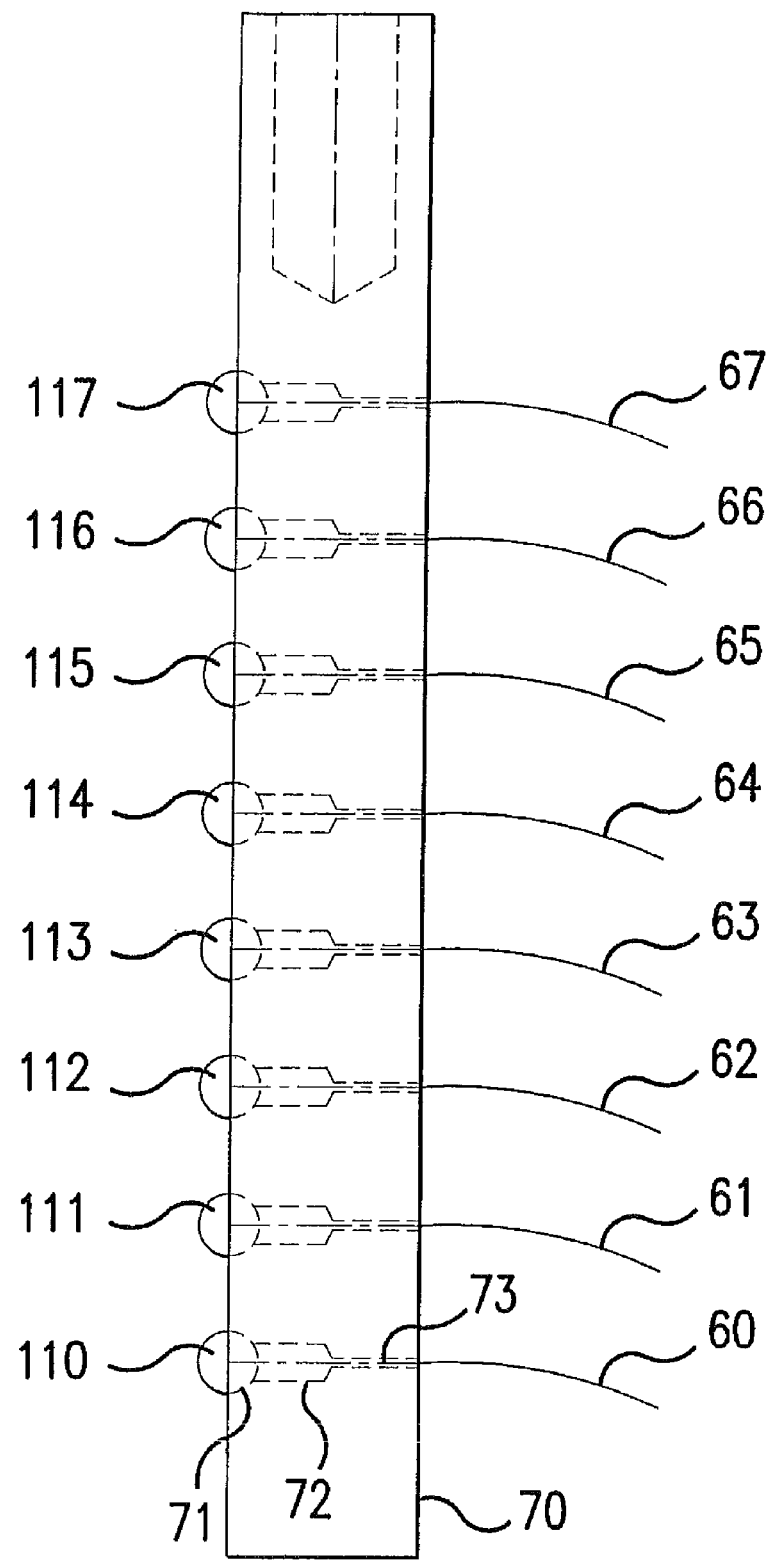

FIGS. 4(a) and (b) are top down and side views of a ball lens holder 70 for eight ball lenses (the eight ball lenses 110-117 are the same as ball lens 110 as shown in FIG. 2(a)). Ball lens holder 70 fixes the ends of the optical fibers 60-67 so that the ends of the optical fiber and the ball lenses 110-117 are separated by a first predetermined distance. Further, the ball lenses are mounted on the ball lens holder, and the ball lens holder 70 is positioned relative to the microchip 100 so that an edge of the ball lenses 110-117 and centers of the microchannels 50-57 are separated by a second predetermined distance, the second predetermined distance being defined as a working distance.

In the illustrated embodiment, the holder 70 is approximately 0.25 inches thick and 0.5 inches wide.

On the upper surface of the holder 70, hemispheric wells 71 are provided to position the each of the ball lenses 110-117, the ball lenses being 5 mm apart from each other. Holes 72 having diameters of 3/64 inches are drilled below each hemispheric well 71 to a depth of 0.140 inches below the upper surface. Further, holes 73 with diameters of approximately 0.011 inches are drilled through the remaining the holder 70 for inserting optical fibers 60-67. The specific dimensions of the holder 70 shown obviously may be varied as may be necessitated by microchips having different channel configurations. Further, the positioning of the ball lenses and the fibers may vary from the specifics described above.

Figure 5A:
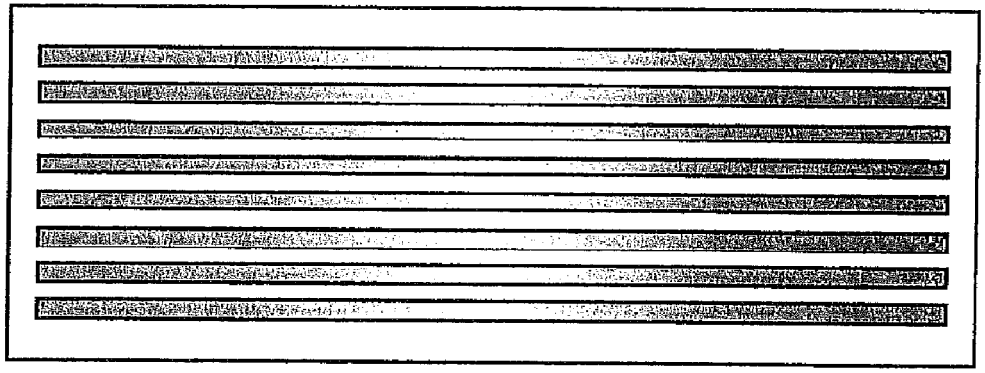
FIG. 5(a) is a schematic of CCD output, with the detected output from eight independent channels arrayed from top to bottom, each with longer wavelength light on the left.
Figure 5B:
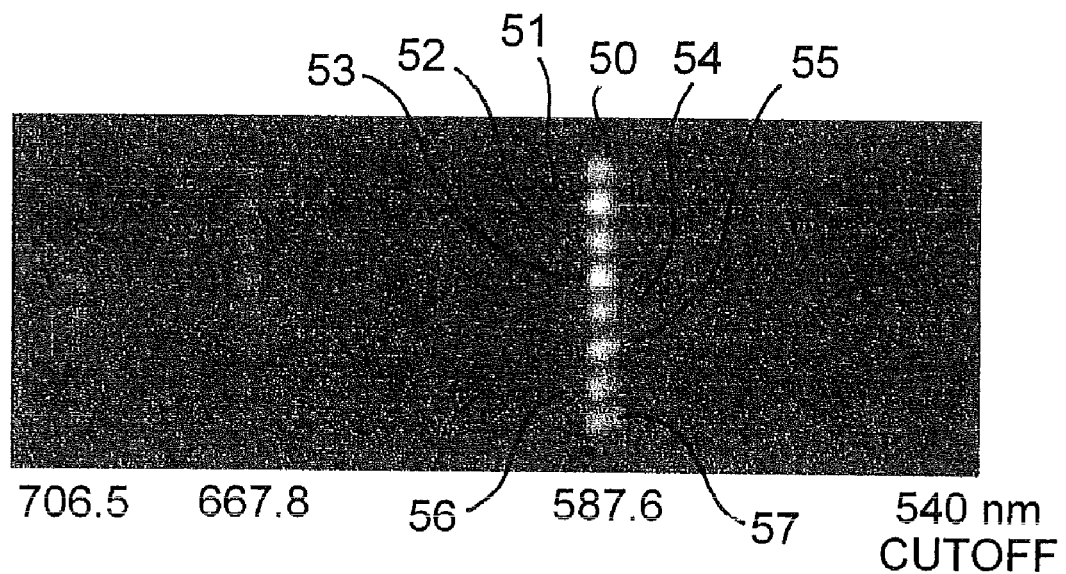
FIG. 5(b) is a demonstration measurement of eight independent spectra with an experimental system of the present invention.

FIGS. 5(a) and (b) show the detected spectra using a multichannel embodiment of the present invention. Specifically, FIG. 5(a) shows a schematic of CCD output, with the output from eight independent channels arrayed from top to bottom, each with longer wavelength light appearing on the left. FIG. 5(b) illustrates the signals from eight fibers taken using a helium gas lamp as a source, showing spectral lines at (left to right) 706.52 nm, 667.82 nm, and 587.56 nm. A 510 nm long pass filter was used in this example.

In particular, FIG. 5(b) illustrates the ability to measure independent spectra simultaneously.

Experimental Results

Figure 6A:
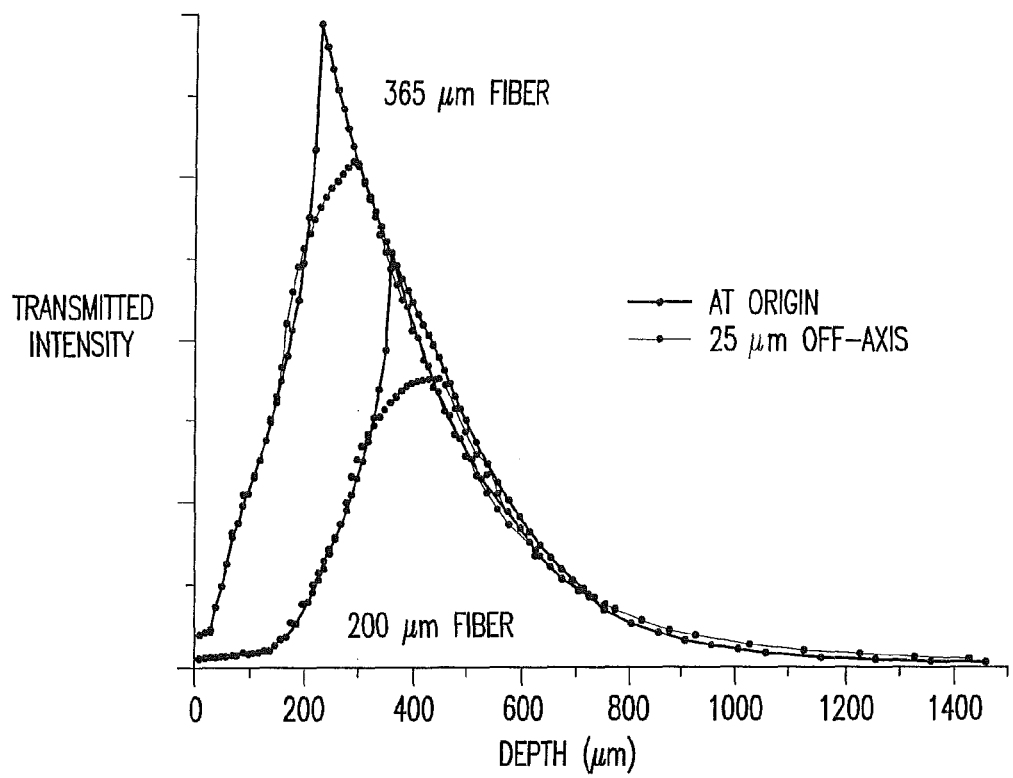
FIGS. 6(a) and (b) show the calculated coupling efficiency of light into the ball lens-fiber system as a function of source position in air, with FIG. 6(a) showing, transmitted intensity as a function of source depth, and FIG. 6(b) showing transmitted intensity as a function of off-axis distance.
Figure 6B:
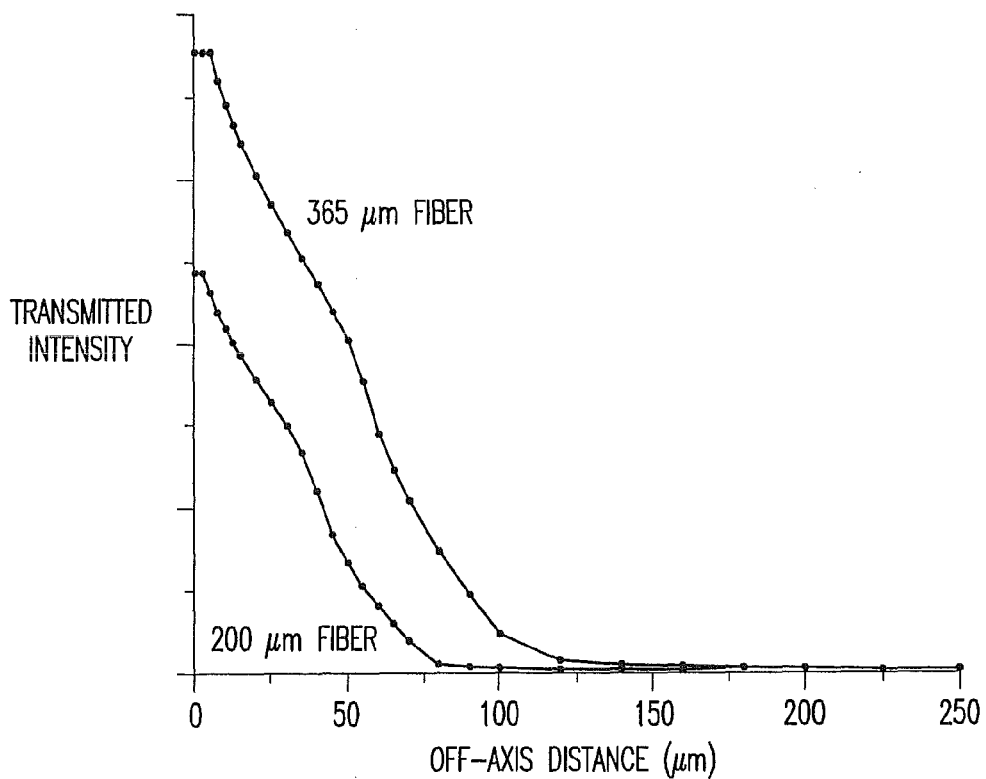
Figure 7:
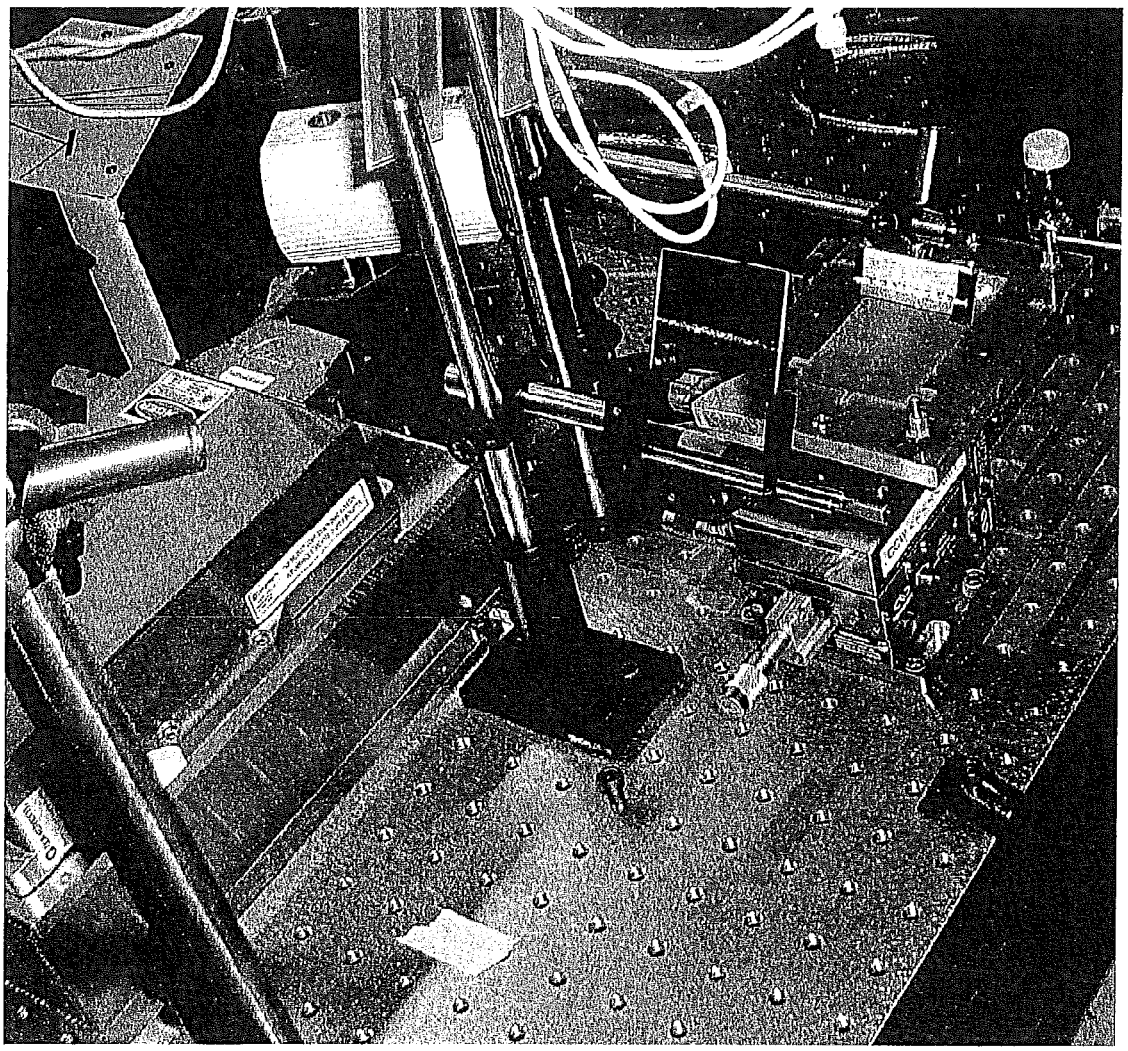
FIG. 7 is an illustration of detection system.
Figure 8:
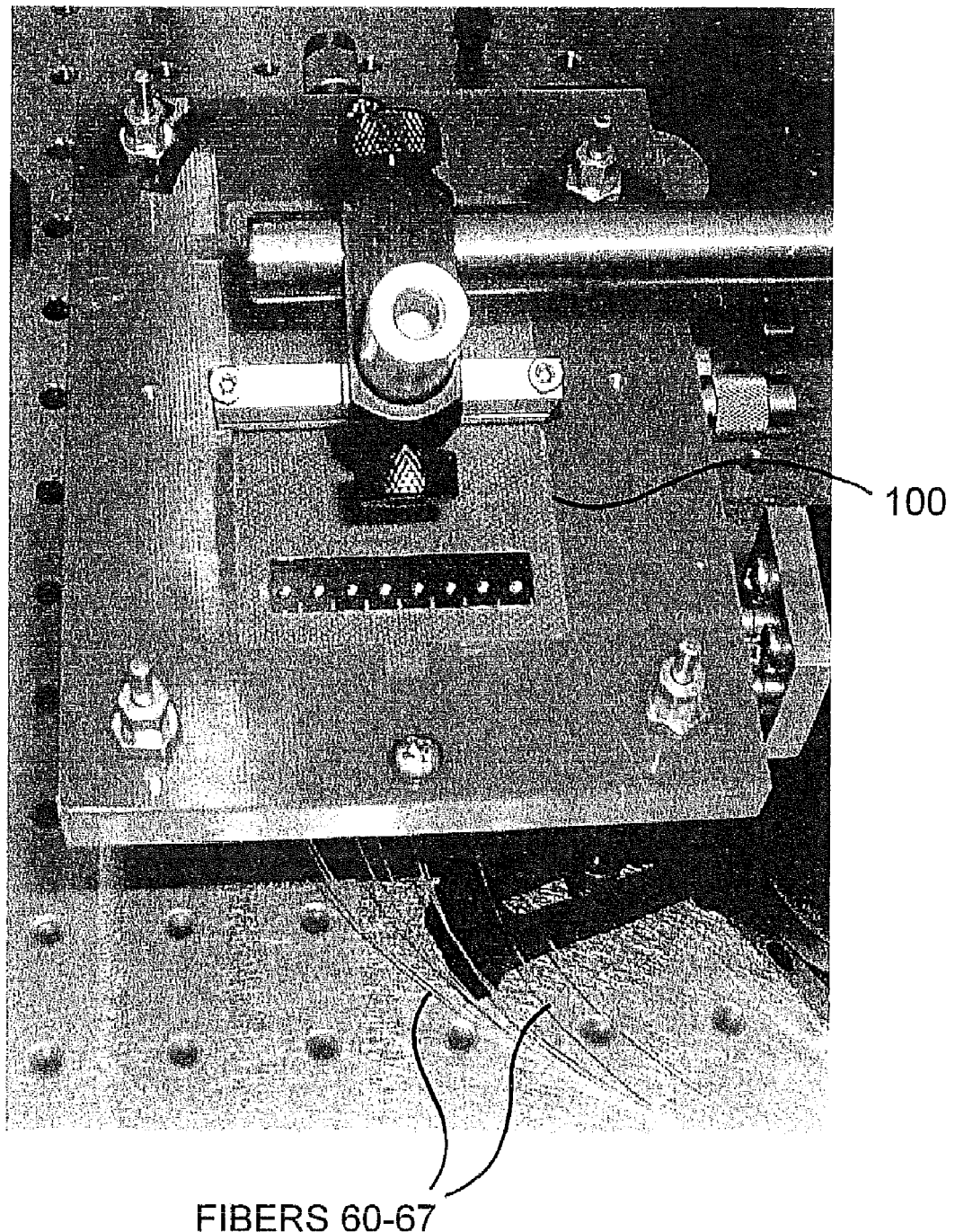
FIG. 8 is another illustration of the detection system.

FIGS. 6(a) and (b) illustrate two examples of the calculated transmitted intensity for light from an isotropically emitting point source collected by a ball lens-optical fiber system in the focusing configuration of FIG. 1(c), as a function of source position in air. In particular, FIG. 6(a) shows the transmitted intensity as a function of source depth, whereas FIG. 6(b) shows the transmitted intensity as a function of the off-axis (lateral) position of the source, where the optical axis is defined by the position of the ball lens and the fiber. Spatial selectivity in the off-axis dimension is primarily determined by the fiber diameter. When using 200 μm diameter fiber with a numerical aperture of 0.22, the optimal fiber-ball lens distance d1 is about 2.4 to 2.6 mm, with greatest collection for a source in air (sample S) approximately 350 to 360 μm distant d2 from the 2 mm ball lens. When using 365 μm fiber, the optimal fiber-ball lens distance d1 is about 3.0 to 3.45 mm, and the optimal source distance in air is approximately 200 to 230 μm distant from the ball lens. These distances must be adjusted for real samples to take into account the index of refraction of the substrate material. The optimal fiber—ball lens distance d1 and the optimal source distance (working distance) d2 are shown in FIG. 1(c).

In general, given a ball lens with a known index of refraction and diameter, and an optical fiber with a known diameter and numerical aperture, the relative positions for optimal collection efficiency can be determined as follows: Treating the sample S as an isotropically emitting point source, the position of the ball lens 110 and optical fiber 60 are such that:

1) the diameter of the circle of least confusion matches the diameter of the fiber, and 2) the marginal ray is at the angular limit of acceptance of the optical fiber (for example, for an optical fiber with 0.22 NA, the marginal ray enters the fiber with an angle of about 12.71 degrees).

The circle of least confusion is defined by the point along the optical axis at which the marginal ray transmitted through the system meets the caustic, or envelope of all transmitted rays, taking spherical aberrations into account. There is a range around the optimal positions where the spatial selection will still be in effect.

For the 200 μm fiber configuration described in FIGS. 6(a) and (b), the calculated numerical aperture is 0.50. On the other hand, for a 365 μm fiber, the NA is 0.62. For a particular diameter and material of ball lens, as the fiber diameter increases, the NA of the system increases, but the spatial selectivity decreases, particularly in the lateral dimension. The spatial selectivity (i.e., the selective collection of light from the region of interest to discriminate against e.g., substrate fluorescence) is shown by the sharp peaks in FIG. 6(a), which also indicates that a detection fiber of 200 μm is well-matched to fluorescence collection from a microchannel of ~100 μm in width, as used in the embodiment of the present invention.

The use of a ball lens and optical fiber in a focused configuration to achieve spatially selective high-numerical aperture collection of fluorescence from a microchannel provides one of the advantages of the present invention.

In applications known in the conventional art, ball lenses are used to couple light into optical fibers by focusing to yield a collimated beam of light of approximately the same diameter as the ball lens, as shown in FIG. 1(b). However, with the present invention, the source (i.e., the microchannel) is moved further away from the ball lens, such that the emitted light converges after passing through the ball lens as shown in FIG. 1(c). As can be seen in FIG. 1(c), by proper positioning of a much smaller diameter fiber where emitted light converges, light originating from the source can be collected much more efficiently than from the surrounding regions, as shown in FIGS. 6(a) and (b). A similar effect could be achieved with a conventional confocal system involving several lenses and a pinhole as shown in FIG. 1(a), but the cost and complexity of alignment for a multichannel system using this technology would be substantially higher.

An additional advantage of the present invention is the larger working distance. For the configuration using a 200 μm diameter fiber and a 2 mm LaSFN9 ball lens, the optimal sample—ball lens distance is 350 to 360 μm in air, compared to less than 90 μm for the collimating configuration (typically used with a larger fiber of the prior art). The larger working distance of the present invention makes it possible to focus the light collecting system at or near the middle of a microchannel in a microfluidic device having a plastic sealing layer which may be 30-50 μm or greater in thickness.

The importance of a larger working distance will become understood by considering the following. First of all, sealing layers are typically required on the microchip in order to have enclosed fluidic channels. However, it is difficult to get a mechanically robust plastic sealing layer thinner than 30-50 μm. A sealing layer having a thickness on the order of 100 μm is mechanically stronger and more stable. For a glass sealing layer, it would difficult to use a sealing layer thinner than a number one cover slip (e.g., 150 μm). Further, diameters of microchannels are typically 20-200 μm (for the present embodiment, the channel heights or thicknesses) are 65 μm). In most analyses, it is desirable to focus at the center of the microchannel. Given the typical microchannel thickness, the center of the channel would be between 40-250 μm from the device surface, even with a plastic sealing layer as thin as 30 µm, which is thinner than the ideal thickness. With a glass-sealing layer, the center of the channel would be between 180-250 µm from the device surface. The index of refraction of the substrates is typically around 1.5 (cover slip glass: 1.51; polycarbonate: 1.59); assuming water in the channel (index of refraction 1.33), this becomes an effective minimum distance between 60 µm and 360 µm in air. Limiting the focal depth to less than 90 µm places severe constraints on device design, both for the material and thickness of the sealing layer as well as for the height or thickness of the microchannel.

Further, the relatively small numerical aperture of the fiber (0.22 NA, or even as low as 0.15) permits efficient coupling of the emitted light into a spectrometer (e.g. a f/2 FICS spectrometer). The numerical aperture of the lens-fiber system can be as high as 0.51 for a 200 µm fiber and 0.62 for a 365 µm fiber with a 2 mm LaSFN9 ball lens.

As still another advantage, the application of the cylindrical lens configuration is used to generate multiple (eight, in the present embodiment) focused spots of light from a single laser beam.

Focusing the light into discrete spots in separate channels rather than scanning the laser over the channels can result in greater power delivery at each channel, as minimal laser power is delivered to the empty areas of the chip. Also dividing the light from a single beam into multiple channels provides internally consistent correction of the fluorescence excitation so that instantaneous output from each channel can be compared without correction for fluctuation in excitation intensity between channels. Also, in a multichannel microfluidic device with electrokinetically driven flow, the need for electrical isolation between the channels can require greater separation than would be ideal for a scanning system, particularly in a polymeric device with a thin sealing layer. In addition, having optical parts that are fixed (i.e., do not move) makes the detection system mechanically more robust than a conventional scanning system.

The combination of an imaging spectrograph and sensitive CCD camera to simultaneously detect multiple spectra has already been extensively used for capillaries and glass microchips, among other applications. The spatially selective, fixed-optics multicolor fluorescence detection system of the present invention makes it possible to detect multiple spectra from plastic microfluidic devices as well, without using a confocal configuration, which has conventionally been required with plastic microfluidic devices. Heretofore, the background fluorescence from the plastic substrate has severely limited sensitivity of fluorescence detection from within a channel without using a confocal configuration. The present invention overcomes this problem.

The spatially selective, fixed-optics multicolor fluorescence detection system may be used for many separation based analyses including but not limited to chromatography and electrophoresis of nucleic acids, proteins, or other molecules of biomedical interest.

The optical detection system of the present invention is independent of any particular microfluidic device, although features of the microfluidic device such as thickness, substrate material, and channel spacing determine some parameters and the alignment of the detection setup.

The laser excitation example shown in FIG. 3(a) includes two cylindrical lenses 20, 21 (a 7 mm wide, 6.35 mm focal length plano-concave lens and a 5 cm wide plano-convex lens with a 30 cm focal length) that are held in standard optical positioners a distance of 30.6 cm apart to generate a 5 cm wide collimated line from the laser beam 10.

From there, the array of eight plano-convex lenses 30-37, each with 5 mm diameter (equal to the channel spacing) and 30 mm focal length in the excitation configuration (leading to a spot size on the order of 30 µm at the focus), breaks the line into eight focused spots 40-47. These plano-convex lenses 30-37 are held in a slot-type holder. Plano-convex lenses 30-37 with a larger focal length would give a smaller spot size; a smaller focal length (smaller than 15 mm, for example) would be hard to accommodate given the angle of incidence for the light on the microfluidic device 100.

For the detection configuration, the ball lenses 110-117 and fibers are held in the holder 70 (refer to FIGS. 4(a) and (b)), which may be made out of black delrin, chosen here for ease of machining and assembly, in that it will not scratch the lenses or the optical fibers, or other suitable material.

Assembly of the detection configuration is as follows, with reference to FIGS. 4(a) and (b). First, fibers 60-67 are cleaved, and the buffer stripped back from a ~5 mm length; then the stripped ends of the fibers 60-67 are inserted into holes 73 of the holder 70, positioned one at a time using a gauge inserted into the top of the holder 70, and glued in place (A room temperature-vulcanizing (RTV) adhesive is one example of suitable adhesive, because it can be removed without damaging the holder. This aspect of RTV is especially suitable for use with prototype detection systems.) The gauge is designed to give the optimal relative positions of the ball lenses and their corresponding fibers. After inserting the fibers 60-67 into holes 73, the RTV can be applied, and then the position of the fibers can be set using the gauge, taking care not to apply any stress on the fibers while the RTV cures. For a detection assembly intended to be more permanent than a prototype assembly, a more durable adhesive, an epoxy for example, could be used instead of RTV. Finally, the ball lenses 110-117 are placed into the hemispheric wells 71 of the holder 70, where they are held in place by gravity, or preferably by a top piece designed and fabricated to capture the outer edges of ball lenses 110-117. One example of a top piece is shown as top piece 70A in FIG. 9, and is described below. The ball lens holder 70, and the microchip are both mounted on XYZ-theta micrometer-controlled stages for alignment purposes and to preserve the ability to measure a variety of microfluidic devices. Once microfluidic device parameters such as material, thickness, channel depth and height or thickness, and lateral size of the chip are optimized, these micrometers can be replaced by more compact but less easily adjustable mounts. The other ends of the fibers 60-67 are held in a 1-D array by a clamshell holder (not shown), which positions the fibers for the introduction of light into the spectrometer 80. In the present embodiment, a 50 mm Nikon lens is used to image the fibers on the entrance of the spectrometer 80. This is done for two reasons: 1) to provide a slight demagnification in order to improve spatial and spectral resolution; and 2) to move the effective slit (the "slit" here is the image of the fiber ends) into the spectrometer slightly, so that the CCD chip on the camera can be slightly further out than the designed image plane of the spectrograph, as it has to be because of the standard C-mount configuration of the camera housing. Modifying the spectrometer to better accommodate the camera could eliminate the need for this lens and further reduce the overall size of the detector assembly. The long pass filter 70 is mounted at the entrance of the spectrometer 80, and the CCD camera 90 is mounted at the exit of the spectrometer 80.

While the one embodiment of a multichannel detection system was described above, numerous variations of the present invention are to be considered within the scope of the present invention.

For example, there are several possible variations for laser excitation. If the spherical plano-convex lenses 30-37 had a longer focal length, the laser spot size would be larger. A variable neutral density filter could be used to make the laser intensity in each of the spots equal (without this correction the spots in the center are brighter than those on the edges). Further, as alternatives to the cylindrical lenses 20, 21, other possibilities include: 1.) using an array of individually aligned custom beam splitters in series to generate multiple spots at any desired set of locations, or 2.) bringing in the laser excitation with another set of optical fibers, also held in a modified version of the fiber-ball lens holder.

Figure 9:
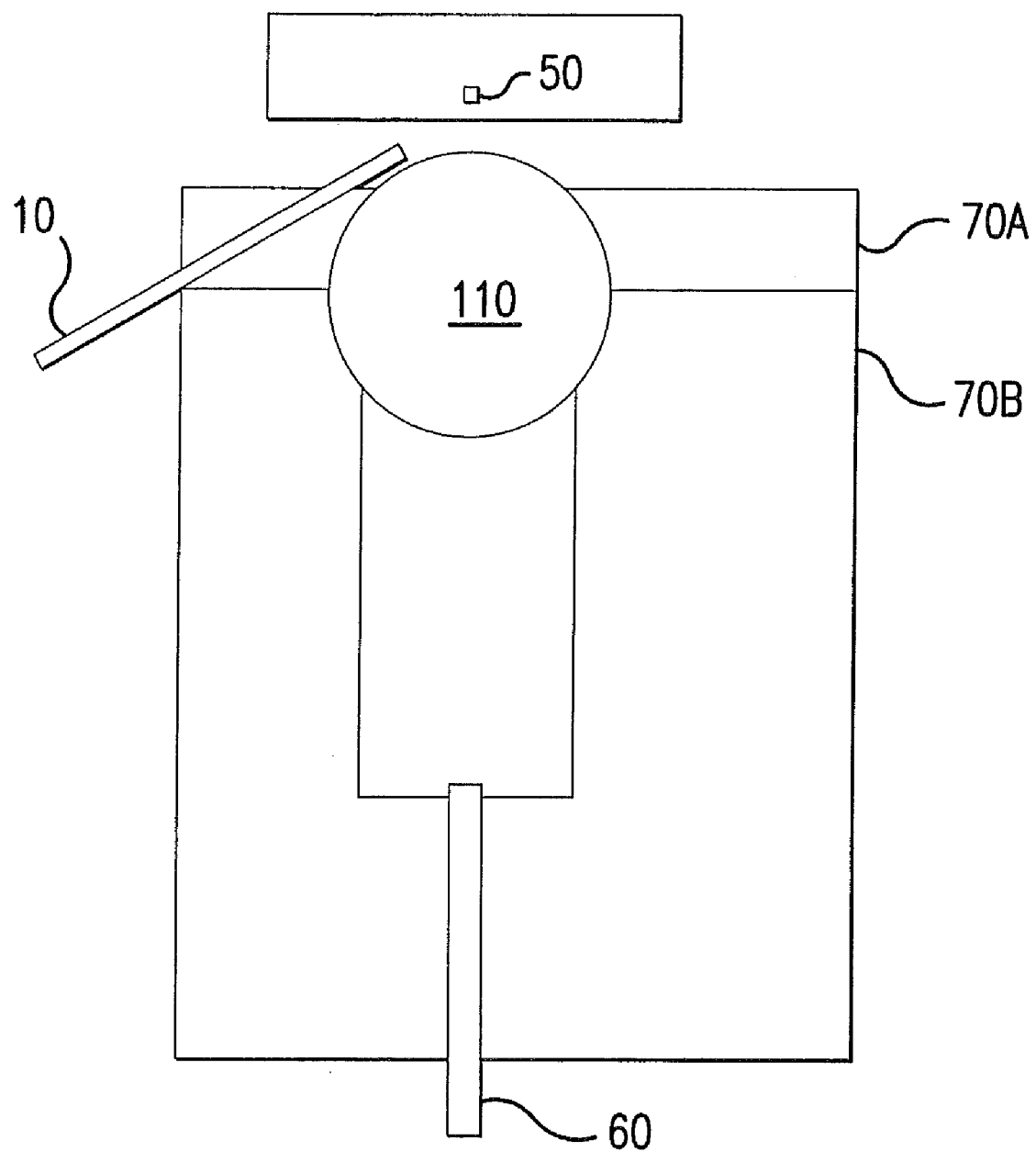
FIG. 9 illustrates an alternative embodiment of laser excitation, with a separate optical fiber for laser excitation incorporated into a variant of the ball lens/detection fiber holder shown in FIGS. 4(a) and (b).

The option 2.) above is shown in FIG. 9. In option 2.), the laser excitation 10 comes in from the same side of the microdevice as the detection apparatus. Laser excitation 10 is brought to the desired location in microchannel 50 using an optical fiber 10, located on the same side of the chip as the detection optics (this arrangement is different than the embodiment shown in FIG. 2(*a*)). In the option shown in FIG. 9 light is collected using a 2 mm ball lens 110 and directed onto the detection optical fiber 60. The fibers and the ball lens are held in a 2-part jig where the bottom piece 70B is nearly identical to the holder 70 described above, and the top piece 70A is used to secure the ball lenses and position the excitation fiber. Because the excitation fiber 10 and detection fiber 60 are in the same holder, the alignment process is simplified. However, reconfiguring the holder pieces 70A and 70B would be required if the channel height or thickness in the microfluidic device were to change, or if the thickness of the channel sealing layer or the material of the channel sealing layer were to change; e.g., if the detector was utilized with different instruments. Nonetheless, the advantages in ease of alignment, compactness, and flexibility of this arrangement may make it desirable once a microfluidic device design is chosen for production.

The detection side of the system may vary in comparison with the embodiment described above. For example, if spectral resolution of multiple wavelengths is not needed, the imaging spectrograph 80 and CCD camera 90 could be replaced by any 1-D array type detector together with the appropriate (e.g., thin-film band pass) filters to select a single spectral region of interest. Such a detector could be a photodiode array, or a set of photomultiplier tubes (one for each channel), or a 1-D CCD array. In this case, freed from the constraint of matching the numerical aperture of the spectrometer, a higher NA fiber could be utilized to get somewhat more spatial selectivity and to collect more light.

In addition, the detection system is effective with a wide variety of polymeric devices, for example devices can be made of poly(carbonate), poly-(methyl methacrylate), poly(styrene), poly(ethylene terephthalate), or other suitable other material.

Further, it should be understood, that each of the excitation system and the detection system described above may be used separately or together, and/or with other devices. Further, the excitation system and/or the detection system described above may be used in conjunction with a flow cell (detection cell), or multiple flow cells, as described in the U.S. Provisional Application No. 60/682,847, entitled Miniature Laser-Induced Fluorescence Detector, filed in the USPTO on May 19, 2005 the entire contents of which are incorporated by reference.

Further, minor changes could be made in the geometry, such as using a smaller diameter optical fiber, which would collect less light but provide greater spatial selectivity. For example, a very small multimode fiber with a core dimension of ~50 μm could be used. Increasing the effective focal length of the ball lenses, either by increasing the diameter of the ball lenses or by reducing the index of refraction, while holding the diameter of the fiber constant gives a larger working distance but less efficient light collection and less spatial selectivity, particularly in the axial direction. An obvious restriction in the size of the ball lenses is that the lenses need to be smaller than the channel separation, the channel separation being 5 mm in the embodiment described above. Using ball lenses with a smaller effective focal length can lead to more efficient light collection as well as greater spatial selectivity, but a smaller working distance. In any case, the distance between the fiber and ball lens, and the distance between the ball lens and the channel center can be optimized according to the principles described herein for maximum light collection.

Further, it is possible to use the same detection apparatus for measuring sample properties other than fluorescence, in particular luminescence.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A spatially selective fluorescence detection system comprising:
    an optical fiber; and
    a ball lens mounted adjacent to one end of the optical fiber for receiving an emitted light from a spatially selected volume, the ball lens having a diameter larger than a diameter of the optical fiber, the ball lens and the one end of the optical fiber being separated by a first distance, the first distance being greater than a radius of the ball lens so that the light emitted from the spatially selected volume and received by the ball lens converges onto the one end of the optical fiber, wherein the first distance from the ball lens to the optical fiber is determined by positioning the spatially selected volume, treated as a point source, relative to the ball lens such that a circle of transmitted light defined by the intersection of a marginal transmitted ray and a caustic has a diameter equal to that of the optical fiber.

2. The detection system according to claim 1, wherein an angle of the marginal transmitted ray as the marginal transmitted ray enters the optical fiber is equal to the maximum acceptance angle of the optical fiber.

3. The detection system of claim 2, wherein a second distance is determined as the distance between the edge of the ball lens and the position of the selected volume by then positioning the selected volume such that the transmitted intensity from the selected volume is maximized.

4. The detection system of claim 1, wherein the selected volume is enclosed is within a microfluidic channel or flow cell, the selected volume having a height and width comparable to those of the microfluidic channel or flow cell, and the microfluidic channel or flow channel being positioned such that light intensity from the selected volume is maximized.

5. The detection system according to claim 1, wherein a diameter of the ball lens is 3 to 40 times the diameter of the optical fiber.

6. The detection system according to claim 4, wherein the diameter of the optical fiber is not more than 10 times greater than a lateral dimension of the microfluidic channel, with the optical fiber providing spatial selectivity in a lateral dimension, wherein the lateral dimension being an off-axis dimension and the lateral dimension being a dimension perpendicular to both the optical fiber and a flow direction of the selected volume at a point of detection.

7. The detection system of claim 1, wherein an effective focal length of the ball lens, given by nD/4(n−1), is less than 1.3 mm, where n=an index of refraction of the ball lens, and D=a diameter of the ball lens.

8. The detection system of claim 1, wherein an effective focal length of the ball lens, given by nD/4(n−1), is less than 2.0 mm, where n=an index of refraction of the ball lens, and D=a diameter of the ball lens.

9. The detection system of claim 1, wherein the optical fiber has a numerical aperture equal to 0.22, or another numerical aperture varying from 0.22 by up to −+10%.

10. The detection system of claim 1, wherein the ball lens has an effective focal length equal to 1.088 mm, or another focal length varying from 1.088 mm by up to +−10%.

11. The detection system of claim 10, wherein the optical fiber has a diameter in a range of 50 µm to 365 µm, and wherein the first distance is in a range of 1.6 mm to 3.45 mm.

12. The detection system of claim 1, wherein the emitted light is fluorescence from the selected volume, where an excitation for fluorescence is brought in off-axis at an angle of 30 degrees to 80 degrees, and wherein the excitation is a laser excitation or other excitation.

13. The detection system of claim 1, further comprising a spectrograph, wherein an end of the optical fiber distal from the ball lens is positioned to direct the emitted light into the spectrograph.

14. The detection system of claim 4, wherein the selected volume is enclosed in a polymeric material.

15. The detection system of claim 4, wherein a center of the selected volume is less than 500 µm from an external surface of the microfluidic device or the flow cell.

16. The detection system of claim 1, wherein the light emitted from the selected volume is focused behind the one end of the optical fiber at points along an axis of the optical fiber.

17. The detection system of claim 4, wherein a lateral dimension of the selected volume is in a range of 50-500 µm.

18. The detection system of claim 3, wherein the second distance is in a range of 60 µm to 360 µm.

19. The detection system of claim 18, wherein a refraction-adjusted second distance, obtained by multiplying the indices of refraction of material between the ball lens and center of the selected volume, is between 100 µm and 360 µm.

20. A spatially selective fluorescence detection system, comprising:

a plurality of optical fibers; and a plurality of ball lenses each mounted adjacent to an end of a respective one of the plurality of optical fibers for receiving an emitted light from one of the plurality of spatially selected volumes, each of the plurality of ball lenses having a diameter larger than a diameter of the respective one of the plurality of optical fibers wherein each of the plurality of ball lenses and one end of the respective one of the plurality of optical fibers being separated by a first distance, the first distance being greater than a radius of the respective one of the plurality of ball lenses so that the emitted light from the plurality of the selected volumes and received by the plurality of ball lenses converges onto the one ends of the plurality of optical fibers, wherein the first distance from each of the plurality of ball lenses to the respective one of the plurality of optical fibers is determined by positioning each of the plurality of selected volumes, each treated as a point source, relative to a respective one of the plurality of ball lenses such that a circle of transmitted light defined by an intersection of the caustic of transmitted rays and a marginal transmitted ray has a diameter equal to that of the respective one of the plurality of optical fibers.

21. The detection system according to claim 20, wherein an angle of the marginal transmitted ray as the marginal transmitted ray enters the respective one of the plurality of the optical fibers is equal to the maximum acceptance angle of the respective one of the plurality of optical fibers.

22. The detection system of claim 20, further comprising an imaging spectrograph, wherein each of the ends of the plurality of optical fibers distal from the plurality of ball lenses is positioned to direct the emitted light from each of the plurality of selected volumes into the spectrograph.

23. The detection system of claim 20, wherein the selected volumes are enclosed within microfluidic channels or flow cells, the selected volumes having heights and widths comparable to those of the microfluidic channels or flow cells, and the microfluidic channels or flow cells being positioned such that light intensities from the selected volumes are maximized.

24. The detection system of claim 23, further comprising a ball lens holder for fixing the one end of the plurality of optical fibers so that the one end of each of the plurality of optical fibers and the respective one of the plurality of ball lenses are separated by the first distance.

25. The detection system of claim 24, wherein each of the plurality of ball lenses is mounted on the ball lens holder, the ball lens holder being positioned relative to the plurality of selected volumes so that an edge of each of the plurality of ball lenses and center of the respective one of the plurality of selected volumes is separated by a second distance.

26. The detection system of claim 25, wherein the second distance is in a range of 60 µm to 360 µm.

27. The detection system of claim 25, wherein a refraction-adjusted second distance, obtained by multiplying the indices of refraction of material between the plurality of ball lenses and centers of the lateral dimensions of the plurality of selected volumes, is between 100 µm and 360 µm.

28. The detection system of claim 25, wherein the ball lens holder includes a top piece and a bottom piece, the plurality of ball lenses being held between the top piece and the bottom piece.

29. The detection system of claim 24, further comprising an excitation fiber mounted on the ball lens holder for each ball lens.

30. A fluorescence detection system for detecting fluorescence of spatially selected volumes from a plurality of spatially selected volumes, comprising:

a pair of cylindrical lenses mounted apart from each other by predetermined distance;

a plurality of plano-convex lenses arranged in a linear array;

a laser emitting a beam of light which passes through the pair of cylindrical lenses and the plurality of plano-convex lenses, the beam of light being split into multiple spots by the plurality of plano-convex lenses, each of the multiple spots being projected toward a different one of the plurality of spatially selected volumes; and a plurality of optical fibers, each of the plurality of optical fibers corresponding to a respective one of the plurality of spatially selected volumes; and a plurality of ball lenses each being positioned adjacent to one end of a respective one of the plurality of optical fibers for receiving an emitted light from the respective one of the spatially selected volumes, each of the plurality of the ball lenses having a diameter larger than a diameter of the respective one of the plurality of optical fibers, each of the plurality of ball lenses and the respective one of the plurality of optical fibers being separated by a first distance, such that the light emitted from each of the plurality of spatially selected volumes and received by the respective one of the plurality of ball lenses converges onto the one end of respective one of the plurality of optical fibers, wherein the first distance from each of the plurality of ball lenses to the respective one of the plurality of optical fibers is determined by positioning each of the plurality of selected volumes, treated as a point source, relative to the respective one of the plurality of ball lenses such that a circle of transmitted light defined by an intersection of the caustic of transmitted rays and a marginal transmitted ray has a diameter equal to that of the respective one of the plurality of optical fibers.

31. The detection system of claim 30, wherein the multiple spots have a diameter equal to 20-50 μm, preferably 20-40 μm, or more preferably 20-30 μm at a focus thereof.

32. The detection system of claim 20, wherein the first distance between each of the plurality of ball lenses and the respective one of the plurality of the optical fibers is in a range of 3 to 40 times the diameter of the respective one of the plurality of optical fibers.

33. A fluorescence detection system for detecting fluorescence from a plurality of spatially selected volumes comprising:
   an excitation laser emitting a beam of light, the beam of light being split into multiple spots by a series of beam splitters, each of the multiple spots being projected toward a different one of the spatially selected volumes;
   a plurality of optical fibers, each of the plurality of optical fibers corresponding to a respective one of the plurality of spatially selected volumes;
   a plurality of ball lenses each being positioned adjacent to one end of a respective one of the plurality of optical fibers for receiving an emitted light from a respective one of the plurality of spatially selected volumes, each of the plurality of ball lenses and the one end of the respective one of the plurality of optical fibers being separated by a first distance, each of the plurality of ball lenses having a diameter larger than a diameter of a respective one of the plurality of optical fibers, wherein the first distance from each of the plurality of ball lenses to the respective one of the plurality of optical fibers is determined by positioning each of the plurality of selected volumes, treated as a point source, relative to a respective one of the plurality of ball lenses such that a circle of transmitted light defined by the intersection of the caustic of transmitted rays and a marginal transmitted ray has a diameter equal to that of the respective one of the plurality of optical fibers, and such that the light emitted from each of the plurality of spatially selected volumes and received by the plurality of ball lenses converges onto the respective one of the plurality of optical fibers; and
   a holder for mounting the plurality of ball lenses, and the plurality of optical fibers.

34. A method for analyzing a plurality of spatially selected volumes by fluorescence, comprising:
   positioning a plurality of ball lenses adjacent to a plurality of spatially selected volumes of a microfluidic device, each of the plurality of ball lenses corresponding to one of the plurality of spatially selected volumes;
   positioning a plurality of optical fibers, each of the plurality of optical fibers corresponding to one of the plurality of ball lenses;
   obtaining simultaneously a fluorescence spectrum from fluorescent substances in the plurality of spatially selected volumes;
   wherein each of the plurality of ball lenses and an end a respective one of the plurality of optical fibers is separated by a first distance, wherein the first distance from each of the plurality of ball lenses to the respective one of the plurality of optical fibers is determined by positioning each of the plurality of selected volumes, treated as a point source, relative to a respective one of the plurality of ball lenses such that a circle of transmitted light defined by an intersection of the caustic of transmitted rays and a marginal transmitted ray has a diameter equal to that of the respective one of the plurality of optical fibers, the first distance being in a range of 3 to 40 times the diameter the respective one of the plurality of optical fibers, so that the light emitted from each of the plurality of spatially selected volumes and received by a respective one of the plurality of ball lenses converges onto the end of the respective one of the plurality of optical fibers.

* * * * *